United States Patent
Reddy Badvel et al.

(10) Patent No.: US 10,250,298 B2
(45) Date of Patent: Apr. 2, 2019

(54) METHOD AND SYSTEM OF COMMUNICATING PERSONAL HEALTH DATA IN A NEAR FIELD COMMUNICATION ENVIRONMENT

(71) Applicant: Samsung Electronics Co., Ltd., Suwon-si, Gyeonggi-do (KR)

(72) Inventors: Jayabharath Reddy Badvel, Bangalore (IN); Thenmozhi Arunan, Bangalore (IN); Eun-Tae Won, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/455,641

(22) Filed: Mar. 10, 2017

(65) Prior Publication Data

US 2017/0187424 A1 Jun. 29, 2017

Related U.S. Application Data

(60) Division of application No. 14/228,923, filed on Mar. 28, 2014, now abandoned, which is a continuation of
(Continued)

(30) Foreign Application Priority Data

Oct. 25, 2010 (IN) .......................... 3173/CHE/2010

(51) Int. Cl.
*H04B 5/00* (2006.01)
*G06Q 10/00* (2012.01)
(Continued)

(52) U.S. Cl.
CPC ........... *H04B 5/0031* (2013.01); *G06F 19/00* (2013.01); *G06F 19/3418* (2013.01);
(Continued)

(58) Field of Classification Search
CPC ....... H04B 5/0031; G06F 12/00; H04W 4/008
See application file for complete search history.

(56) References Cited

U.S. PATENT DOCUMENTS 7,032,079 B1   4/2006 Bauman et al.
8,244,917 B2 *  8/2012 Takayama ............. H04W 36/14
                                                    710/1
(Continued)

FOREIGN PATENT DOCUMENTS

EP     2 573 970 A2    3/2013
WO     2009/068931 A1  6/2009
WO     2010/077194 A1  7/2010

OTHER PUBLICATIONS

Digital Signature Records for the NFC Data Exchange format. Michael Ronald. Pub Date: Apr. 1, 2010.*
(Continued)

*Primary Examiner* — Md K Talukder
(74) *Attorney, Agent, or Firm* — Jefferson IP Law, LLP

(57) ABSTRACT

A method and a system for communicating personal health data in a Near Field Communication (NFC) environment are provided. An NFC manager sets control information in an NFC Data Exchange Format (NDEF) for providing synchronized communication of personal health data between the NFC manager and an NFC agent. The control information may include a direction flag, a state flag, sequence identifier field, and request/response flag. The NFC manager writes the NDEF format including the control information and payload data into an NFC tag associated with the NFC agent. Subsequently, the NFC manager reads the NDEF record stored in the NFC tag and determines whether the NDEF record is written into the NFC tag by the NFC agent based on the control information in the read NDEF format.
(Continued)

Accordingly, the NFC manager repeats the above mentioned steps if the NDEF record includes payload data of the NFC agent.

14 Claims, 5 Drawing Sheets

Related U.S. Application Data application No. 13/881,661, filed as application No. PCT/KR2011/007981 on Oct. 25, 2011, now Pat. No. 10,148,318.

(51) Int. Cl.
*G06Q 50/24* (2012.01)
*G06F 19/00* (2018.01)
*G16H 10/60* (2018.01)
*H04W 4/80* (2018.01)
*A61B 5/00* (2006.01)

(52) U.S. Cl.
CPC ............ *G06Q 10/00* (2013.01); *G06Q 50/24* (2013.01); *G16H 10/60* (2018.01); *H04W 4/80* (2018.02); *A61B 5/0015* (2013.01)

(56) References Cited

U.S. PATENT DOCUMENTS

| | | | |
|---|---|---|---|
| 8,527,987 B2* | 9/2013 | Johansson | G06F 8/61 717/178 |
| 2004/0203342 A1* | 10/2004 | Sibecas | H04B 7/2606 455/11.1 |
| 2004/0210624 A1* | 10/2004 | Andrzejak | H04L 29/06 709/201 |
| 2006/0043179 A1* | 3/2006 | Nycz | A61B 50/33 235/385 |
| 2006/0061482 A1 | 3/2006 | Monney et al. | |
| 2006/0183462 A1* | 8/2006 | Kolehmainen | H04B 5/00 455/411 |
| 2007/0120650 A1* | 5/2007 | Nagai | G06K 7/0008 340/10.2 |
| 2007/0138302 A1* | 6/2007 | Antoniou | H04L 41/00 235/492 |
| 2007/0210162 A1 | 9/2007 | Keen et al. | |
| 2007/0263595 A1* | 11/2007 | Charrat | H04L 45/00 370/351 |
| 2008/0079547 A1* | 4/2008 | Alicot | G06K 7/0008 340/10.3 |
| 2008/0162312 A1 | 7/2008 | Sklovsky et al. | |
| 2008/0220878 A1 | 9/2008 | Michaelis | |
| 2008/0252415 A1 | 10/2008 | Larson et al. | |
| 2008/0288958 A1* | 11/2008 | Ryoo | G06F 9/54 719/313 |
| 2009/0119190 A1* | 5/2009 | Realini | G06Q 20/04 705/30 |
| 2009/0147803 A1* | 6/2009 | Takayama | G06K 7/0008 370/475 |
| 2009/0222659 A1 | 9/2009 | Miyabayashi et al. | |
| 2009/0248437 A1 | 10/2009 | Gucciardi et al. | |
| 2009/0282130 A1* | 11/2009 | Antoniou | H04L 41/0886 709/220 |
| 2010/0004950 A1 | 1/2010 | Bajko et al. | |
| 2010/0017570 A1* | 1/2010 | Gallo | G06K 7/10237 711/154 |
| 2010/0041332 A1 | 2/2010 | Flygh et al. | |
| 2010/0045425 A1* | 2/2010 | Chivallier | A61B 5/0002 340/5.8 |
| 2010/0090810 A1* | 4/2010 | Gallo | G06Q 20/04 340/10.51 |
| 2010/0161352 A1* | 6/2010 | Lim | A61B 5/0002 705/3 |
| 2010/0169686 A1* | 7/2010 | Ryoo | G06F 9/54 713/323 |
| 2010/0178868 A1* | 7/2010 | Charrat | G06Q 20/3278 455/41.1 |
| 2010/0313034 A1 | 12/2010 | Senshu et al. | |
| 2011/0109443 A1 | 5/2011 | Kaga et al. | |
| 2011/0276975 A1* | 11/2011 | Brown | G06F 3/162 718/103 |
| 2012/0077593 A1* | 3/2012 | Sarmenta | A63F 3/00643 463/40 |
| 2013/0032687 A1* | 2/2013 | Zhang | G06F 1/187 248/544 |
| 2013/0065521 A1 | 3/2013 | Jang et al. | |
| 2013/0132687 A1* | 5/2013 | Gallo | G06K 7/10237 711/154 |
| 2013/0217329 A1* | 8/2013 | Reddy Badvel | G06Q 10/00 455/41.1 |
| 2013/0241709 A1* | 9/2013 | Tiedemann | H04L 1/0079 340/10.42 |
| 2013/0314334 A1 | 11/2013 | Leica et al. | |
| 2013/0344804 A1 | 12/2013 | Chen et al. | |
| 2014/0185088 A1* | 7/2014 | Lee | H04N 1/00342 358/1.15 |
| 2014/0213182 A1* | 7/2014 | Reddy Badvel | G06Q 10/00 455/41.1 |
| 2014/0213183 A1* | 7/2014 | Reddy Badvel | G06Q 10/00 455/41.1 |
| 2014/0256251 A1* | 9/2014 | Caceres | H04B 5/0031 455/41.1 |
| 2017/0187424 A1* | 6/2017 | Reddy Badvel | G06Q 10/00 |

OTHER PUBLICATIONS

Bravo et al.; Supporting Clinical Information Management by NFC Technology; Nov. 23, 2008; XP009136887; Castilla-La Mancha University; Spain.

IEEE; Health Informatics—Personal Health Device Communication Part 20601: Application ProfileOptimized Exchange Protocol; IEEE Std 11073-20601-2008; Dec. 19, 2008; XP017604162; IEEE Engineering in Medicine and Biology Society; New York.

Android NDEF Push Protocol Specification; Feb. 22, 2011; XP055163343; Version 1.

NFC Forum; Simple NDEF Exchange Protocol—Technical Specification, SNEP 1.0; Aug. 31, 2011; XP055081363.

* cited by examiner

300

| MB | MB | MB | MB | MB | TNF |
|----|----|----|----|----|-----|
| TYPE LENGTH ||||||
| PAYLOAD LENGTH 3 ||||||
| PAYLOAD LENGTH 2 ||||||
| PAYLOAD LENGTH 1 ||||||
| PAYLOAD LENGTH 0 ||||||
| ID LENGTH ||||||
| TYPE ||||||
| ID ||||||
| PAYLOAD (304) ||||||

FIG.3A

| DATA-PROTO-ID | PROTOCOL VERSION | ENCODING RULES | NOMENCLATURE VERSION | SYSTEM IDENTIFIER LENGTH | SYSTEM IDENTIFIER | CONFIG-REPORT LENGTH | CONFIG-REPORT DATA | MEASUREMENT DATA LENGTH | MEASUREMENT DATA |
|---|---|---|---|---|---|---|---|---|---|
| 402 | 404 | 406 | 408 | 410 | 412 | 414 | 416 | 418 | 420 |

METHOD AND SYSTEM OF COMMUNICATING PERSONAL HEALTH DATA IN A NEAR FIELD COMMUNICATION ENVIRONMENT

PRIORITY

This application is a divisional application of prior application Ser. No. 14/228,923, filed on Mar. 28, 2014 application, which is a continuation of prior application Ser. No. 13/881,661 which is a National Stage application under 35 U.S.C. § 371 of an International application filed on Oct. 25, 2011 and assigned application No. PCT/KR2011/007981, which claims the benefit under 35 U.S.C. § 365(b) of an Indian patent application filed on Oct. 25, 2010 in the Indian Intellectual Property Office and assigned Serial No. 3173/CHE/2010, the entire disclosures of which are hereby incorporated by reference.

BACKGROUND OF THE INVENTION

1. Field of the Invention

The present invention relates to the field of near field communication system. More particularly, the present invention relates to a method and system of communicating personal health data in a near field communication environment.

2. Description of the Related Art

Near Field Communication (NFC) is used in devices for communicating with other devices in a network range of less than 10 cm. Typically, in an NFC system, user applications can read or write information from or to NFC tags. NFC tags are static in nature and do not have capabilities for dynamically processing of data stored in it. Generally, NFC tags are powered by a radio frequency field generated by an active NFC device and are able to respond to requests from the active NFC device.

A standard developed by the International Organization for Standardization (ISO) and the Institute of Electrical and Electronics Engineers (IEEE) referred to as ISO/IEEE 11073 enables communication between medical devices and external systems. Personal health devices that are complaint with ISO/IEEE 11073 standards can communicate with each other using the ISO/IEEE 11073-20601 communication protocol. The ISO/IEEE 11073 standard defines an 'agent' as a node that collects and transmits personal health data to an associated NFC manager and 'manager' as a node that receives personal health data from one or more agents. Exemplary managers include a cell phone, a health appliance, a set top box, a personal computer system and the like. The ISO/IEEE 11073-20601 standard defines the communication protocol between the NFC agent and the NFC manager.

Typically, an NFC manager (i.e., ISO/IEEE 11073 manager with an NFC Read/Write Interface) and an NFC agent (i.e., ISO/IEEE 11073 agent with an NFC tag) communicate in an NFC reader/writer mode using an NFC Data Exchange Format (NDEF) message. The NDEF message can be any one of type, text, a Uniform Resource Indicator (URI), an image, a Multipurpose Internet Mail Extensions (MIME) type, etc. In the NFC reader/writer communication mode, NDEF messages are exchanged between the NFC manager and the NFC agent using the tag transport protocols.

Generally, the NFC agent and NFC manager exchange a sequence of ISO/IEEE 11073-20601 Application Protocol Data Units (APDUs) for association, configuration and exchanging of measurement data. This involves series of request and response exchanges between the NFC agent and the NFC manager.

Usually, when an NFC manager writes a request into an NFC tag residing in an NFC agent, the NFC agent reads the request stored in the NFC tag and writes a response to the request into the NFC tag. The NFC manager reads the response written by the NFC agent from the NFC tag. However, in the event that the NFC agent delays the reading of the request from the NFC tag, the NFC manager reads the request written by itself and considers the request as a response from the NFC agent due to the limited capabilities of the NFC tag, leading to connection setup latency and communication overhead.

The above information is presented as background information only to assist with an understanding of the present disclosure. No determination has been made, and no assertion is made, as to whether any of the above might be applicable as prior art with regard to the present invention.

SUMMARY OF THE INVENTION

Aspects of the present invention are to address at least the above-mentioned problems and/or disadvantages and to provide at least the advantages described below. Accordingly, an aspect of the present invention is to provide a method and system for communicating personal health data in a Near Field Communication (NFC) environment.

In accordance with an aspect of the present invention, a method of communicating personal health data in an NFC environment is provided. The method includes setting control information in an NFC Data Exchange Format (NDEF) record by a first NFC device to synchronize communication between the first NFC device and a second NFC device in the NFC environment, wherein the control information includes at least one of a direction flag, a request/response type flag, a state flag and a sequence identifier field, and writing the NDEF record containing the control information into an NFC tag.

In accordance with another aspect of the present invention, an apparatus for communicating personal health data in an NFC environment is provided. The apparatus includes a processor, and memory coupled to the processor, wherein the memory comprises a read/write module configured for setting control information in an NFC Data Exchange Format (NDEF) record, wherein the control information includes a direction flag, a request/response type flag, a state flag and a sequence identifier field, and writing the NDEF record containing the control information into an NFC tag.

The present invention is to provide a method and system for communicating personal health data in an NFC environment.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF DRAWINGS

The above and other aspects, features, and advantages of certain exemplary embodiments of the present invention will be more apparent from the following description taken in conjunction with the accompanying drawings, in which:

FIG. 3A is a schematic representation of an NDEF record according to an exemplary embodiment of the present invention.

FIG. 4 is a schematic representation of a payload field in the NDEF record according to another exemplary embodiment of the present invention.

Throughout the drawings, it should be noted that like reference numbers are used to depict the same or similar elements, features, and structures.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
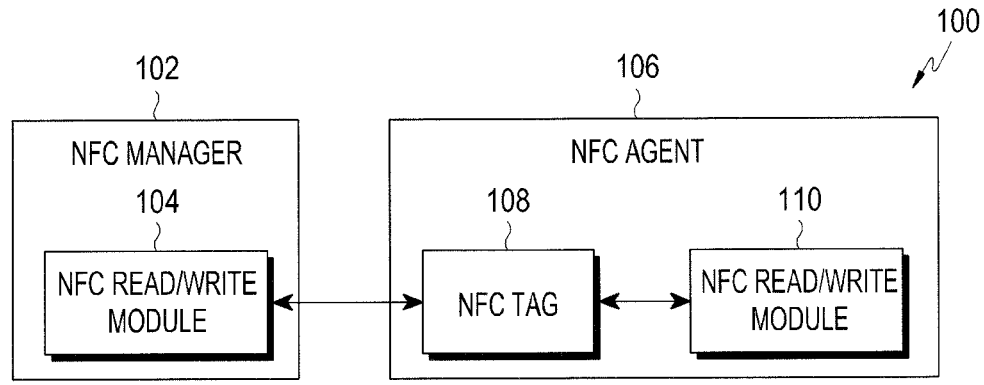
FIG. 1 is a block diagram of a Near Field Communication (NFC) system enabling communication of personal health data between an NFC manager and an NFC agent according to an exemplary embodiment of the present invention.

FIG. 1 is a block diagram 100 of a Near Field Communication (NFC) system for enabling communication of personal health data between an NFC manager and an NFC agent according to an exemplary embodiment of present invention.

Referring to FIG. 1, the NFC system 100 includes an NFC manager 102 having an NFC read/write module 104, and an NFC agent 106 with an NFC tag 108 and an NFC read/write module 110. The NFC manager 102 may be a device (e.g., a cell phone, a tablet, a smart phone, a personal digital assistant, a set-top box, a personal computer, and the like) capable of communicating with the NFC agent 106. The NFC agent 106 is a device capable of collecting personal health data and communicating the personal health data with the NFC manager 102 via the NFC tag 108. The NFC manager 102 and the NFC agent 106 writes and/or reads data in the NFC tag 108 using a standard developed International Organization for Standardization (ISO) and Institute of Electrical and Electronics Engineers (IEEE) referred to as the ISO/IEEE 11073-20601 communication protocol.

For communicating personal health data, the NFC manager 102 and the NFC agent 106 exchange a series of request/response messages via the NFC tag 108. In an exemplary operation, the NFC manager 102 sets control information in a NFC Data Exchange Format (NDEF) record. The NDEF record may contain a header and a payload field. The payload field includes control information and/or other payload data. It is noted that the control information can be encoded in other fields of the NDEF record other than the payload field. The control information may include a direction flag, a state flag, a request/response flag, and a sequence identifier field. The direction flag indicates a direction of communication of the NDEF record. The state flag indicates a state of communication of the NFC manager 102 or the NFC agent 106. The request/response flag indicates whether the NDEF record carries an ISO/IEEE 11073-20601 protocol request command or an ISO/IEEE 11073-20601 protocol response command. The sequence identifier field indicates a sequence identifier of NDEF records exchanged between the NFC manager 102 and the NFC agent 106. According to the exemplary embodiment, the control information is set in the NDEF record to provide synchronized communication between the NFC manager 102 and the NFC agent 106 to efficiently obtain personal health data from the NFC agent 106. Upon the setting of the control information, the NFC read/write module 104 of the NFC manager 102 writes the NDEF record containing the control information and/or other payload data into the NFC tag 108.

Subsequently, the NFC read/write module 110 of the NFC agent 106 reads the NDEF record stored in the NFC tag 108. The NFC read/write module 110 retrieves the control information from the NDEF record and determines a direction of the communication, a request/response command, a communication state, and a sequence identifier based on the direction flag, a request/response flag, a state flag, and a sequence identifier field. In the above case, the direction flag indicates if the direction of communication is from the NFC manger 102 to the NFC agent 106 or vice-versa. The request/response flag indicates if the NDEF record carries the request command in the payload field. The state flag indicates the communication state of the NFC manager when the NDEF record is written in the NFC tag 108. The sequence identifier field indicates the sequence identifier allocated to the NDEF record by the NFC agent. Accordingly, the NFC read/write module 110 updates the control information (i.e., the direction flag, the sequence identifier, the state flag and the request/response flag) in the NDEF record and encodes payload data in the payload field of the NDEF record. Then, the NFC read/write module 110 writes the NDEF record into the NFC tag 108.

At substantially the same time, the NFC read/write module 104 of the NFC manager 102 reads the NDEF record containing the control information and other payload data from the NFC tag 108. The NFC read/write module 104 then retrieves the control information from the NDEF record and determines a direction of the communication, a request/response command, a communication state, and a sequence identifier based on the direction flag, the request/response flag, the state flag, and the sequence identifier field. Accordingly, the NFC read/write module 104 determines whether the NDEF record read from the NFC tag 108 is same as the previous NDEF record written into the NFC tag 108 based on the control information in the read NDEF record. For example, if the direction flag indicates the direction of communication as from the NFC manager 102 to the NFC agent 106 and the request/response flag indicates that the NDEF records contain the request command, then the NFC read/write module 104 identifies that the NDEF record is the same NDEF record previously written by the NFC manager 102 and is not the NDEF record received from the NFC agent 106. In such a scenario, the read/write module 104 may ignore the read NDEF record and continue reading the NFC tag 108 after a time interval. That is, the NDEF record read by the NFC read/write module 104 is the same as the previously written NDEF record and the NDEF record written into the NFC tag 108 is not yet read by the NFC agent 106 or the NFC read/write module 104 has read the NFC tag 108 prior to writing the NDEF record by the NFC agent 106. In such a case, the control information in the NDEF record enables the NFC manager 102 to determine the identity of the NDEF record.

If the NFC read/write module 104 determines that the NDEF record contains payload data previously received from the NFC agent 106, then the NFC read/write module 104 processes the payload data and encodes new control information and different payload data in an NDEF record. Then, the NFC read/write module 104 writes the NDEF record with the new control information and different payload data in the NFC tag 108. The above process continues until personal health data is communicated to the NFC manager 102 by the NFC agent 106 in the payload field of one of the NDEF records exchanged between the NFC manager 102 and the NFC agent 106.

Figure 2:
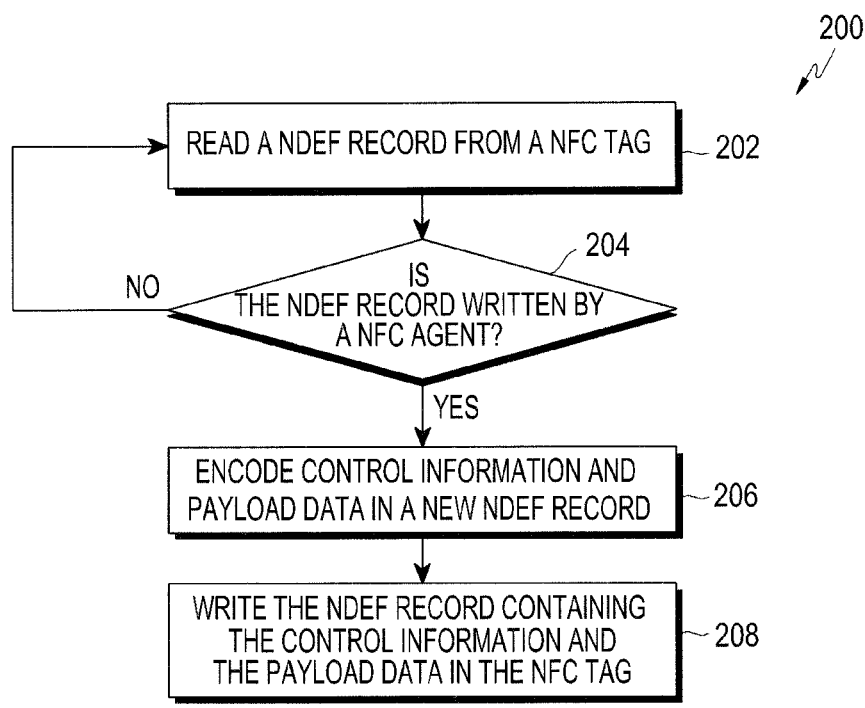
FIG. 2 is a flowchart illustrating a method of reading/writing NFC Data Exchange Format (NDEF) record into the NFC tag according to an exemplary embodiment of the present invention.

FIG. 2 is a flowchart illustrating a method of reading/writing NFC Data Exchange Format (NDEF) record into the NFC tag according to an exemplary embodiment of present invention.

Referring to FIG. 2 of the flowchart 200, at step 202, an NDEF record containing the control information and payload data is read from the NFC tag 108. As described above, the control information includes a direction flag, a state flag, a request/response flag, and a sequence identifier field. At step 204, it is determined whether the NDEF record in the NFC tag 108 is written by the NFC agent 106 based on the control information. If the NDEF record is written by the NFC agent 106, then at step 206, the payload data in the read NDEF record is processed and new control information and payload data (e.g., ISO/IEEE 11073-20601 data) is encoded in the payload field of a new NDEF record. At step 208, the new NDEF record containing the control information and the payload is written into the NFC tag 108. Steps 202-208 are repeated until a complete ISO/IEEE 11073 personal health data payload is received from the NFC agent 106. Referring back to step 204, if the NDEF record is written by the NFC manager 102, then the NDEF record is ignored and the NFC tag 108 is read again after a time to obtain another NDEF record. One skilled in the art will realize that the above steps 202-208 can also be implemented at the NFC agent 106.

FIG. 3A is a schematic representation of an NDEF record according to an exemplary embodiment of present invention.

The NFC record 300 includes a payload field 302. The payload field 302 includes control information associated with the NDEF record and other payload data. Alternatively, an ID field 304 includes control information associated with the NDEF record. The NDEF record 300 can be exchanged between the NFC manager 102 and the NFC agent 106 in a peer-to-peer mode using a Simple NDEF Exchange Protocol (SNEP). For example, the NFC manager 102 acting as a SNEP client can exchange the NDEF record 300 with the NFC agent 106 acting as SNEP server. For this, the NFC manager 102 can use a SNEP request message with a PUT request to send the NDEF record 300 to the NFC agent 106. The NFC agent 106 can send a response NDEF record to the NFC manager 102 using a SNEP response message with a PUT request. Alternatively, the NFC manager 102 can use a SNEP request message with a GET request.

Figure 3B:
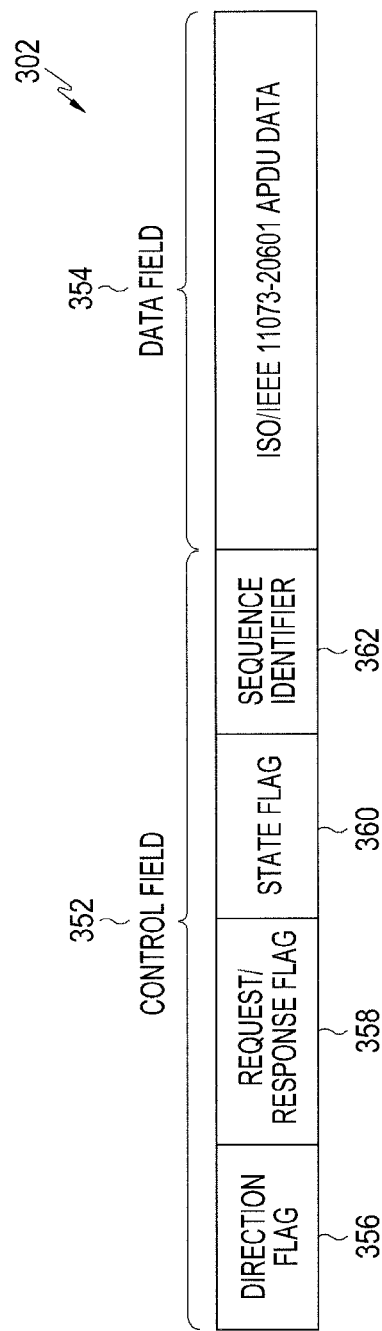
FIG. 3B is a schematic representation of a payload field in the NDEF record according to an exemplary embodiment of the present invention.

FIG. 3B is a schematic representation of the payload field in the NDEF record, according to an exemplary embodiment of present invention.

The payload field 302 in the NDEF record 300 includes a control field 352 and a data field 354. The control field 352 includes a direction flag field 356, a request/response flag field 358, a state flag field 360, and a sequence identifier field 362. The direction flag field 356 indicates a direction of communication of the NDEF record. For example, the direction flag field 356 includes a value '0' if the NDEF record is written into the NFC tag 108 by the NFC agent 106. When the NDEF record is written by the NFC manager 102, the direction flag field 356 includes a value '1'.

The request/response flag field 358 indicates whether the NDEF format includes an ISO/IEEE 11073-20601 communication protocol request command or ISO/IEEE 11073-20601 communication protocol response command. For example, the request/response flag field 358 includes a value '0' when the NDEF record corresponds to a request command and includes a value '1' when the NDEF record corresponds to a response command. The state flag field 360 indicates a communication state of a sender of the NDEF record. The state flag field 360 helps determine the state of the NFC manager 102 or the NFC agent 106 during a particular instance of communication. Exemplary values of the state flag field 360 indicate a specific state of the NFC manager 102 or the NFC agent 106 as shown in Table 1 below:

TABLE 1

| | |
|---|---|
| 0x00 | DISCONNECTED |
| 0x01 | CONNECTED |
| 0x02 | UNASSOCIATED |
| 0x03 | ASSOCIATING |
| 0x04 | ASSOCIATED |
| 0x05 | OPERATING |
| 0x06 | CONFIGURING |
| 0x07 | DISASSOCIATING |
| 0x08-0X3F | RFU |

For example, as shown in Table 1, the state flag field 360 may include a value '0x00' when the NFC agent 106 or the NFC manager 102 is in a disconnected state. When the NFC agent 106 or the NFC manager 102 is in a connected state, the state flag field 362 may include a value '0x01'.

The sequence identifier field 362 indicates a sequence identifier assigned to each NDEF record communicated between the NFC read/write module 104/110 and the NFC tag 108. In other words, the sequence identifier field 362 indicates the order in which the NDEF records are written into the NFC tag so that the NDEF records are not duplicated or missed during communication between the NFC manager 102 and the NFC agent 106. The sequence identifier that is exchanged between the NFC manager 102 and the NFC agent 106 can be a random number or a sequence of numbers incremented by one.

The sequence identifier field 362 enables the controlling of the flow of NDEF records exchanged between the NFC read/write module 104/110 and the NFC tag 108. The sequence identifier in the sequence identifier field 362 provides reliability in communication between the NFC manager 102 and the NFC agent 106. It is noted that the sequence field 362 can also be included in a header of the NDEF record. The data field 354 includes ISO/IEEE 11073-20601 data exchanged between the NFC manager 102 and the NFC agent 106.

FIG. 4 is a schematic representation of the payload field of the NDEF record, according to another exemplary embodiment of present invention.

The payload field 302 is used for communicating measurement data (e.g., physical health data). The payload field 302 encodes ISO/IEEE 11073-20601 personal health information, thereby enabling interoperability in exchanging ISO/IEEE 11073 personal health data. The payload field 302 reduces connection setup latency and communication overhead.

The payload field 302 includes a data proto-id field 402, a protocol version field 404, an encoding rules field 406, a nomenclature version field 408, a system identifier length field 410, a system identifier field 412, a config-report length field 414, a config-report data field 416, a measurement data length field 418, and a measurement data field 420.

The data proto-id field 402 indicates an identifier of a data exchange protocol. For example, the data proto-id field 402 includes a value '0', '20601' and '65535'. The value '20601' indicates that the ISO/IEEE 11073-20601 protocol is used. The protocol version field 404 is a one byte field indicating protocol identifier version used by the NFC agent 106. For example, the 4 Most Significant Bits (MSB) indicate a major release version and the 4 Least Significant Bits (LSB) indicate a minor release version. The encoding rules field 406 indicates specific data Application Protocol Data Units (APDU) encoding rule(s) that are supported by the NFC agent 106. It is appreciated that, the NFC agent 106 and the NFC manager 102 supports Medical Device Encoding Rules (MDER) and negotiates on other encoding rule(s) except MDER. For example, the encoding rules field 406 includes a value '0' if MDER is supported, a value '1' if eXtensible markup language Encoding Rules (XER) are supported, and a value '2' if Packed Encoding Rules (PER) are supported.

The nomenclature version field 408 indicates a version of nomenclature used as defined in ISO/IEEE 11073-20601. For example, the MSB bit is set to a value '0' if the nomenclature version 1 is used. The system identifier length field 410 indicates a length of the system identifier field 412. The system identifier field 412 includes a unique system identifier of the NFC agent 106. The Extended Unique Identifier-64 (EUI-64) format is used to identify the NFC agent 106. The system identifier field 412 enables the NFC manager 102 to determine the identity of the NFC agent 106 and to implement a simple access restriction policy.

The config-report length field 414 indicates a length of the config-report data field 416. The config-report data field 416 carries a configuration event report of the NFC agent 106 starting with object handling bytes. The format of the config-report data field 416 is similar to the configuration event report as specified in the ISO/IEEE 11073-20601 specification. The measurement data length 418 indicates a length of the measurement data field 420. The measurement data field 420 carries a measurement data report from the NFC agent 106 starting with object handle bytes. The format of the measurement data field 420 is similar to the measurement data report as specified in ISO/IEEE 11073-20601 specification.

Figure 5:
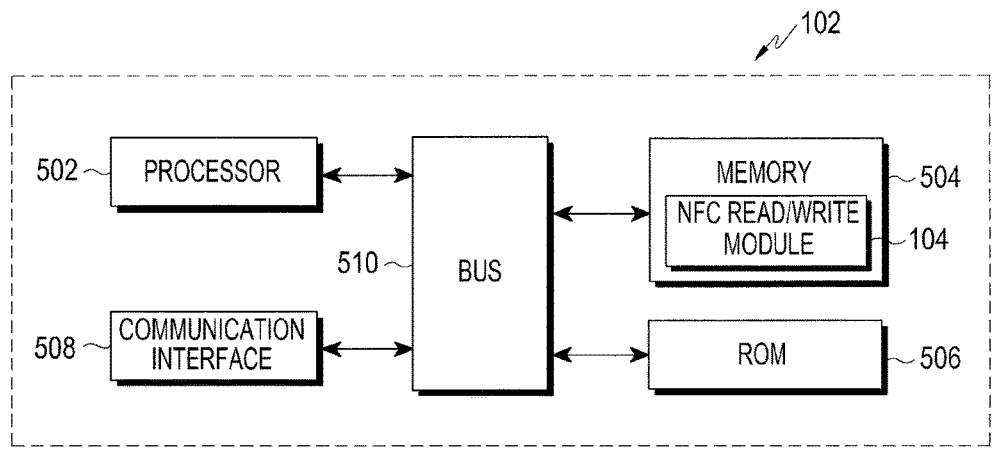
FIG. 5 illustrates a block diagram of the NFC manager according to an exemplary embodiment of the present invention.

FIG. 5 illustrates a block diagram of the NFC manager according to an exemplary embodiment of the present invention.

Referring to FIG. 5, the NFC manager 102 includes a processor 502, memory 504, a Read Only Memory (ROM) 506, a communication interface 508, and a bus 510. The processor 502, as used herein, can be implemented by any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other type of suitable processing circuit. The processor 502 may also include embedded controllers, such as generic or programmable logic devices or arrays, application specific integrated circuits, single-chip computers, smart cards, and the like.

The memory 504 may be volatile memory and non-volatile memory. The memory 504 includes the NFC read/write module 104 for reading and/or writing NDEF records containing control information and other payload data from and/or to the NFC tag 108, according to an exemplary embodiment of the present invention. The communication interface 508 may be a radio frequency interface for enabling communication between the NFC Manager 102 and the NFC Agent 106 in a peer-to-peer mode, a reader and/or writer mode, and a card emulation mode. The bus 510 enables communication between the various components of the NFC manager 102 illustrated therein.

Exemplary embodiments of the present invention may be implemented in conjunction with modules, including functions, procedures, data structures, and application programs, for performing tasks, or defining data types or low-level hardware contexts. Machine-readable instructions stored on any of the above-mentioned storage media may be executable by the processor 502. For example, a computer program may include machine-readable instructions capable of reading and/or writing NDEF records containing control information and other payload data from and/or to the NFC tag 108, according to the exemplary embodiment of the present invention. In an exemplary embodiment, the computer program may be included on a storage medium and loaded from the storage medium to a hard drive in the non-volatile memory.

Figure 6:
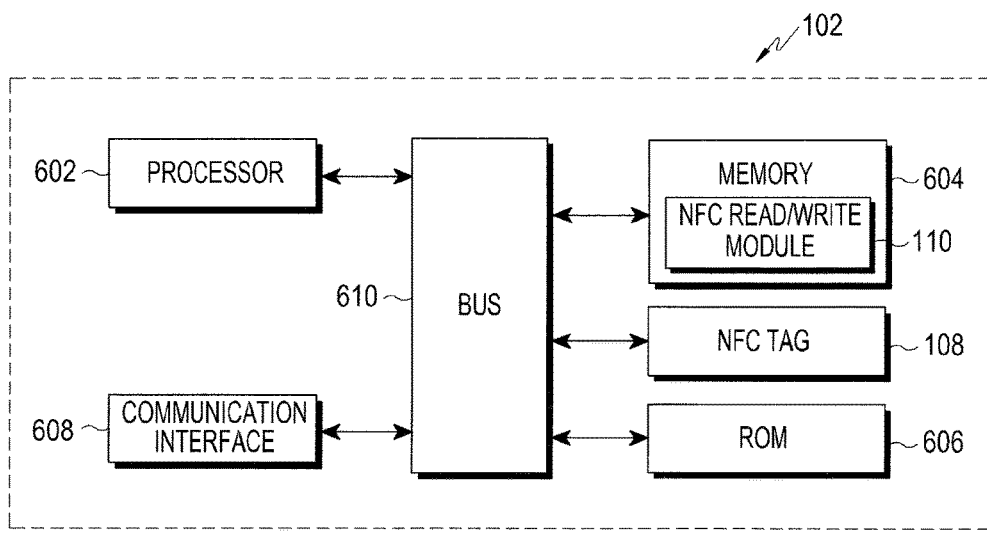
FIG. 6 illustrates a block diagram of the NFC agent according to an exemplary embodiment of the present invention.

FIG. 6 illustrates a block diagram of the NFC agent according to an exemplary embodiment of the present invention.

Referring to FIG. 6, the NFC agent 106 includes the NFC tag 108, a processor 602, memory 604, a ROM 606, a communication interface 608, and a bus 610. The processor 602, as used herein, can be implemented by any type of computational circuit, such as, but not limited to, a microprocessor, a microcontroller, a complex instruction set computing microprocessor, a reduced instruction set computing microprocessor, a very long instruction word microprocessor, an explicitly parallel instruction computing microprocessor, a graphics processor, a digital signal processor, or any other suitable type of processing circuit. The processor 602 may also include embedded controllers, such as generic or programmable logic devices or arrays, application specific integrated circuits, single-chip computers, smart cards, and the like.

The memory 604 may be volatile memory and non-volatile memory. The memory 604 includes the NFC read/write module 110 for reading and/or writing NDEF records containing control information and other payload data from and/or to the NFC tag 108, according to an exemplary embodiment of the present invention. The communication interface 608 may be a radio frequency interface for enabling communication between the NFC manager 102 and the NFC agent 106 in a peer-to-peer mode, a reader and/or writer mode, and a card emulation mode. The bus 610 enables communication between the various components of the NFC agent 106 illustrated therein.

Exemplary embodiments of the present invention may be implemented in conjunction with modules, including functions, procedures, data structures, and application programs, for performing tasks, or defining data types or low-level hardware contexts. Machine-readable instructions stored on any of the above-mentioned storage media may be executable by the processor 602. For example, a computer program may include machine-readable instructions capable of reading and/or writing NDEF records containing control information and other payload data from and/or to the NFC tag 108 and communicating the NDEF records stored in the NFC tag into the NFC manger 102, according to the exemplary embodiment of the present invention. In an exemplary embodiment, the computer program may be included on a storage medium and loaded from the storage medium to a hard drive in the non-volatile memory.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. A method for transmitting and receiving data by a Near Field Communication (NFC) manager in a NFC environment, the method comprising:
    reading, by a processor of the NFC manager, a first NFC Data Exchange Format (NDEF) message from a NFC tag embedded in a NFC agent;
    checking, by the processor, a direction flag in a control field of the first NDEF message; and
    when the direction flag of the first NDEF message indicates that the first NDEF message is directed to the NFC manger, writing, by the processor, a second NDEF message in which the direction flag indicates that the second NDEF message is directed to the NFC agent.

2. The method of claim 1, further comprising:
    determining, by the processor, whether the direction flag of the first NDEF message indicates that the NFC agent communicates with another device; and
    when the direction flag of the first NDEF message indicates that the NFC agent communicates with the other device, terminating an NFC communication with the NFC agent.

3. The method of claim 1, wherein, when the direction flag is 0, a corresponding NDEF message is directed to the NFC manager.

4. The method of claim 1, wherein, when the direction flag is 1, a corresponding NDEF message is directed to the NFC agent.

5. The method of claim 1, wherein the control field further includes a request/response flag and a status flag.

6. The method of claim 5, wherein the status flag indicates a status of the NFC communication.

7. The method of claim 5, further comprising determining whether the request/response flag corresponds to 0 or 1,
    wherein, when the request/response flag corresponds to 0, a corresponding NDEF message includes an ISO/IEEE 11073-20601 protocol request command, and
    wherein, when the request/response flag corresponds to 1, the corresponding NDEF message includes an ISO/IEEE 11073-20601 protocol response command.

8. A Near Field Communication (NFC) manager for transmitting and receiving data in a NFC environment, the NFC manager comprising:
    a communication interface; and
    a processor configured to:
        read a first NFC Data Exchange Format (NDEF) message from a NFC tag embedded in an NFC agent,
        check a direction flag in a control field of the first NDEF message, and
        when the direction flag of the first NDEF message indicates the first NDEF message is directed to the NFC manger, write a second NDEF message in which the direction flag indicates that the second NDEF message is directed to the NFC agent.

9. The NFC manager of claim 8, wherein the processor is further configured to:
    determine whether the direction flag of the first NDEF message indicates that the NFC agent communicates with another device, and
    when the direction flag of the first NDEF message indicates that the NFC agent communicates with the other device, terminate an NFC communication.

10. The NFC manager of claim 8, wherein, when the direction flag is 0, a corresponding NDEF message is directed to the NFC manager.

11. The NFC manager of claim 8, wherein, when the direction flag is 1, a corresponding NDEF message is directed to the NFC agent.

12. The NFC manager of claim 8, wherein the control field further includes a request/response flag and a status flag.

13. The NFC manager of claim 12, wherein the status flag indicates a status of the NFC communication.

14. The NFC manager of claim 12,
    wherein the processor is further configured to determine whether the request/response flag corresponds to 0 or 1,
    wherein, when the request/response flag corresponds to 0, a corresponding NDEF message includes an ISO/IEEE 11073-20601 protocol request command, and
    wherein, when the request/response flag corresponds to 1, the corresponding NDEF message includes an ISO/IEEE 11073-20601 protocol response command.

* * * * *